United States Patent [19]

Rine

[11] Patent Number: 5,738,879
[45] Date of Patent: Apr. 14, 1998

[54] SCALP HAIR TREATMENT METHOD AND COMPOSITION

[76] Inventor: Jasper M. Rine, 1438 N. Forest Ave., River Forest, Ill. 60305

[21] Appl. No.: 751,090

[22] Filed: Nov. 15, 1996

[51] Int. Cl.$^6$ ........................................ A61K 7/06
[52] U.S. Cl. .................. 424/70.8; 424/70.1; 424/401; 424/682; 424/697; 514/864; 514/880; 514/881
[58] Field of Search .................... 424/401, 70.1, 424/70.8, 682, 697; 514/864, 880, 881

[56] References Cited

U.S. PATENT DOCUMENTS 4,968,685  11/1990  Grollier ................................ 514/256

*Primary Examiner*—Jyothsan Venkat
*Attorney, Agent, or Firm*—McDonnell Boehnen Hulbert & Berghoff

[57] ABSTRACT

A scalp and hair treatment method and composition wherein the composition comprises deionized water, a vasodilator (such as ethyl nicotinate and/or capsicum extract), a magnesium salt, and a hydrolyzed protein. The composition can be applied on a monthly or bi-monthly basis to the scalp and hair for about 30 minutes and rinsed away with water.

8 Claims, No Drawings

5,738,879

SCALP HAIR TREATMENT METHOD AND COMPOSITION

The provisional application for the present invention was filed on Nov. 15, 1995 as Ser. No. 60/006,766 now abandoned. This invention is a unique scalp and hair treatment method and composition. Specifically, the present invention provides a unique composition that exfoliates dry skin and opens skin pores to cleanse the scalp and remove excess sebum. Further, the composition of the present invention provides complex nutrients which nourish the shaft of hair. Humectants and botanicals soothe and stimulate the scalp and hair to bring back the natural vitality and radiance of hair. In addition, Vitamins $B_6$, $B_{12}$, C, and E penetrate deeply through the hair cuticles to restore essential moisture and provide enrichment benefits to the hair shaft. The most preferred embodiment of the composition of the present invention is provided in Table I. In the preferred embodiment, the composition comprises deionized water, a vasodilator, and a magnesium salt. Further in the preferred embodiment, the vasodilator is either ethyl nicotinate and/or capsicum extract, and the magnesium salt is magnesium sulfate and/or magnesium citrate. Those of skill in the art will recognize that other ingredients can be incorporated. For example, a hydrolyzed protein can also be incorporated, as well as panthanol. In the preferred embodiment, the hydrolyzed protein is hydrolyzed keratin.

In the composition of the preferred embodiment, the weight percentage of the ethyl nicotinate is about 0.10–0.50%, the percentage by weight of the hydrolyzed keratin is about 0.01–10.00%, the percentage by weight of the magnesium sulfate is about 0.05–4.00%, the percentage by weight of the panthenol is about 0.10–5.00%, the percentage by weight of the magnesium citrate is about 0.10–6.00%, and the percentage by weight of the safflower oil and capsicum extract is about 0.01–2.5% when added together, and the percentage by weight of the capsicum extract alone is about 0.01–0.10%.

The method of the present invention contemplates use of the composition of the present invention as desired. For example, it is contemplated that the composition of the present invention be used on a monthly or bi-monthly basis. In the preferred method embodiment, the composition of the present invention is gently massaged into the scalp and hair and then combed through the hair. Next a thermogenetic cap is placed over the scalp and hair for about 30 minutes. The cap is then removed and the scalp and hair is rinsed thoroughly with water. Further in the preferred embodiment, a moisturizer is applied to the scalp and hair for about 3 minutes and then rinsed away thoroughly with water.

TABLE I

SCALP AND HAIR TREATMENT COMPOSITION
Percentage Formula

|  | % By Weight |
|---|---|
| Deionized Water | 73.8121% |
| Algin | 1.7000 |
| Magnesium Sulfate | 2.0000 |
| Panthenol | 1.0000 |
| Cetyl Alcohol | 0.5000 |
| Stearyl Alcohol | 0.5000 |
| Glyceryl Stearate and polyethylene glycol-100 Stearate | 0.5000 |
| Methylparaben | 0.2000 |
| Propylparaben | 0.1000 |
| Phenoxyethanol | 0.6000 |
| Soyaethyl Morpholinium Ethosulfate | 0.2500 |

TABLE I-continued

SCALP AND HAIR TREATMENT COMPOSITION
Percentage Formula

|  | % By Weight |
|---|---|
| Hydrolyzed Keratin | 6.6000 |
| PPG-5-Ceteth-20 | 1.2500 |
| Dimethylpabamido Laurdimonium Tosylate and Propylene Glycol Stearate | 1.0000 |
| Magnesium Citrate | 4.5000 |
| Methylchloroisothiazolinone and Methylisothiazolinone | 0.0500 |
| Cyanocobalamin (Vitamin $B_{12}$) | 0.0010 |
| Papain | 0.0100 |
| Pyridoxine Hydrochloric Acid (Vitamin $B_6$) | 0.0100 |
| Ascorbic Acid (Vitamin C) | 0.0100 |
| Magnesium Carbonate | 0.0100 |
| Benzalkonium Chloride | 0.1000 |
| Propylene Glycol and Balm Mint Extract | 0.1000 |
| Propylene Glycol and Rosemary Extract | 0.1000 |
| Dimethicone Copolyol | 1.0000 |
| Safflower Oil and Capsicum Extract | 0.0400 |
| Tocopheryl Acetate (Vitamin E) | 0.1000 |
| Ethyl Nicotinate | 0.0400 |
| Fragrance | 0.2500 |
| Menthol | 0.0500 |
| Diammonium Copper EDTA | 0.0169 |
| Triethanolamine | 3.6000 |
| Ext. D&C Violet No. 2 | quantity sufficient |
| FD&C Yellow No. 6 | quantity sufficient |
| FD&C Red No. 40 | quantity sufficient |
|  | 100.0000% |

The foregoing detailed description of the invention has been made in general terms and with respect to the preferred embodiment. The preferred method and composition stated herein may be varied by persons skilled in the art without departing from the spirit and scope of the present invention as set forth in the following claims and equivalents.

What is claimed:

1. In a scalp and hair treatment the improvement comprising a vasodilator selected from the group consisting of ethyl nicotinate, capsicum extract and mixtures thereof, wherein the percentage by weight of the ethyl nicotinate is between about 0.10% and about 0.50%, and wherein the percentage by weight of the capsicum extract is between about 0.01% and about 0.10%, and an effective amount of a magnesium salt to stimulate blood flow, in combination with a hydrolyzed protein.

2. The improved scalp and hair treatment of claim 1, wherein the magnesium salt comprises magnesium sulfate or magnesium citrate, or mixtures thereof, and wherein the percentage by weight of the magnesium sulfate is between about 0.05% and about 4.00%, and wherein the percentage by weight of the magnesium citrate is between about 0.10% and about 6.00%.

3. The improved scalp and hair treatment composition of claim 1, wherein the hydrolyzed protein is hydrolyzed keratin and wherein the percentage by weight of the hydrolyzed keratin is between about 0.01% and about 10.00%.

4. The improved scalp and hair treatment composition of claim 1 further comprising panthenol, wherein the percentage by weight of the panthenol is between about 0.10% and about 5.00%.

5. A method of treating the scalp and hair comprising the steps of:

(a) massaging into the scalp and hair the improved scalp and hair treatment composition of claim 4;

(b) combing the scalp and hair; and (c) rinsing thoroughly the improved scalp and hair treatment composition away from the scalp and hair with water.

6. The method of claim 5 further comprising the step of applying a moisturizer to the scalp and hair for about 3 minutes and then rinsing the moisturizer away thoroughly with water.

7. The method of claim 5 further comprising placing a thermogenic cap over the scalp and hair for about 30 minutes after the step of combing the scalp and hair, removing the thermogenic cap and rinsing the scalp and hair thoroughly with water.

8. The method of claim 7 further comprising the step of applying a moisturizer to the scalp and hair for about 3 minutes and then rinsing the moisturizer away thoroughly with water.

* * * * *